(12) United States Patent
Collin et al.

(10) Patent No.: US 6,325,994 B1
(45) Date of Patent: Dec. 4, 2001

(54) COSMETIC COMPOSITION COMPRISING A STYRENE/ACRYLATE COPOLYMER AND A FATTY PHASE

(75) Inventors: Nathalie Collin, Sceaux; Sophie Bodelin, Vanves, both of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/477,823

(22) Filed: Jan. 5, 2000

(30) Foreign Application Priority Data

Jan. 6, 1999 (FR) .................................................. 99 00055

(51) Int. Cl.$^7$ .......................... A61K 7/021; A61K 7/025; A61K 7/42

(52) U.S. Cl. .............................. 424/63; 424/401; 424/64; 424/59

(58) Field of Search ................................ 424/401, 59, 63, 424/64, 70.1, 70.11, 70.6, 70.16, 70.7, 70.9

(56) References Cited

U.S. PATENT DOCUMENTS

| | | |
|---|---|---|
| 4,423,031 | 12/1983 | Murui et al. . |
| 4,489,058 | 12/1984 | Lay et al. . |
| 5,496,905 | 3/1996 | Gindre et al. . |
| 5,632,998 | * 5/1997 | Midha et al. . |
| 5,662,892 | 9/1997 | Bolich, Jr. et al. . |
| 5,874,072 | * 2/1999 | Alwattari et al. . |

FOREIGN PATENT DOCUMENTS

| | | |
|---|---|---|
| 0 568 035 | 11/1993 | (EP) . |
| 0 665 234 | 8/1995 | (EP) . |
| 0 749 746 | 12/1996 | (EP) . |
| 0 749 747 | 12/1996 | (EP) . |
| 96/33690 | 10/1996 | (WO) . |

OTHER PUBLICATIONS

Derwent Publications Ltd., London, GB; XP002115141 (JP 08 198729) (1996).
Patent Abstracts of Japan, vol. 096, No. 002, Feb. 29, 1996 (JP 07 252115).
English language Derwent Abstract of EP 0 665 234 (1995).
English language Derwent Abstract of EP 0 749 746 (1996).
English language Derwent Abstract of EP 0 749 747 (1996).

* cited by examiner

Primary Examiner—Thurman K. Page
Assistant Examiner—Brian K. Seidleck
(74) Attorney, Agent, or Firm—Finnegan, Henderson, Farabow, Garrett & Dunner, L.L.P.

(57) ABSTRACT

A composition for topical application comprising, in a cosmetically, dermatologically, hygienically or pharmaceutically acceptable support, at least one fatty phase and at least one lipophilic polymer, wherein the lipophilic polymer is a tert-butylstyrene/$C_1$–$C_{10}$ alkyl methacrylate/$C_1$–$C_{10}$ alkyl acrylate copolymer. The composition makes it possible to obtain a film which has very good staying power and good transfer-resistance properties. The film obtained is particularly resistant to water, to rubbing, for example with the fingers or against clothing, to perspiration and to sebum.

55 Claims, No Drawings

COSMETIC COMPOSITION COMPRISING A STYRENE/ACRYLATE COPOLYMER AND A FATTY PHASE

The present invention relates to a composition containing at least one styrene/acrylate copolymer, which is intended in particular for the cosmetics, dermatological, pharmaceutical and hygiene fields. More specifically, the invention relates to a composition for caring for or making up the skin, including the lips, or alternatively superficial keratinous body growths, such as the eyelashes, the eyebrows, the hair and the nails.

This composition can be in the form of a mascara, an eyeliner, a product for the lips, a face powder, an eyeshadow, a foundation, a make-up product for the body, a concealer product, an antisun composition, a skin-coloring composition or a skincare product.

Products for making up or caring for the human skin or lips, such as eyeliners, foundations or lipsticks, or alternatively for the eyelashes, such as mascaras, generally contain fatty substances, such as waxes and oils, pigments and/or fillers and, optionally, additives such as cosmetic or dermatological active agents. When these compositions are applied to the skin or the eyelashes, they leave a film on them which does not always have good water-resistance, during bathing or taking a shower, for example, and/or resistance to tears, to perspiration or to sebum, and/or to rubbing with the fingers or against clothes. The film is thus made brittle and the make-up effect resultantly does not have good staying power over time.

Moreover, these compositions also have the drawback of transferring, i.e., of becoming at least partly deposited, leaving marks on certain supports with which they may come into contact, in particular a glass, a cup, a cigarette, an item of clothing or the skin. This results in mediocre persistence of the film applied, making it necessary to freshen the application of the make-up composition regularly. Moreover, the appearance of unacceptable marks, in particular on shirt collars, may dissuade some women from using this type of make-up.

One object of the present invention is to develop a composition which does not have the above drawbacks and which leads to the formation of a film which has good staying power and is resistant to water.

The inventors have discovered, entirely surprisingly, that the use of a specific styrene/acrylate copolymer in a cosmetic, dermatological, pharmaceutical or hygiene composition can make it possible to obtain a film which has very good staying power and good transfer-resistant properties. The film obtained is resistant in particular to water, to rubbing, for example with the fingers or against clothing, to perspiration and to sebum. The film is also supple, flexible, shiny and non-sticky.

More specifically, a subject of the present invention is a composition for topical application comprising, in a cosmetically, dermatologically, hygienically or pharmaceutically acceptable support, at least one fatty phase and at least one lipophilic polymer, characterized in that the lipophilic polymer is a tert-butylstyrene/$C_1$–$C_{10}$ alkyl methacrylate/$C_1$–$C_{10}$ alkyl acrylate copolymer.

Another subject of the invention is the use, in a cosmetic, dermatological or hygiene composition or for the manufacture of a pharmaceutical composition for topical application, of at least one tert-butylstyrene/$C_1$–$C_{10}$ alkyl methacrylate/$C_1$–$C_{10}$ alkyl acrylate copolymer to obtain a film which has good staying power and/or which is resistant to water, to rubbing, to perspiration and/or to sebum, and/or which has transfer-resistance properties, whereas the composition comprises at least one fatty phase.

A subject of the invention is also a cosmetic process for making up or for non-therapeutically treating the skin or superficial keratinous body growths, which includes applying thereto a composition as described above.

The expression "lipophilic polymer" means a polymer which can be dissolved and/or dispersed in the fatty phase of the composition.

Preferably, the lipophilic polymer is a copolymer of tert-butylstyrene/$C_1$–$C_{10}$ alkyl methacrylate/$C_1$–$C_{10}$ alkyl acrylate and of a vinylaromatic monomer other than tert-butylstyrene.

Advantageously, the lipophilic polymer can be a copolymer derived from the polymerization of:
a) 10 to 55% by weight, relative to the total weight of monomers, of para-tert-butylstyrene,
b) 20 to 80% by weight of $C_1$–$C_{10}$ alkyl methacrylate monomer,
c) 2 to 25% by weight of $C_1$–$C_{10}$ alkyl acrylate monomer,
d) from 0 to 40% by weight of vinylaromatic monomer other than para-tert-butylstyrene.

The alkyl group of the $C_1$–$C_{10}$ alkyl methacrylate monomer can be linear or branched and preferably contains from 1 to 4 carbon atoms, and more preferably contains 4 carbon atoms. $C_1$–$C_{10}$ alkyl methacrylates which may be mentioned, for example, are methyl methacrylate, ethyl methacrylate, propyl methacrylate, isobutyl methacrylate and n-butyl methacrylate. The methacrylate monomer which is particularly preferred is isobutyl methacrylate.

The alkyl group of the $C_1$–$C_{10}$ alkyl acrylate monomer can be linear or branched and can preferably contain from 2 to 8 carbon atoms, and more preferably contains 8 carbon atoms. $C_1$–$C_{10}$ alkyl acrylates which may be mentioned, for example, are propyl acrylate, isopropyl acrylate, n-butyl acrylate, isobutyl acrylate, pentyl acrylate, hexyl acrylate and 2-ethylhexyl acrylate. The acrylate monomer which is particularly preferred is 2-ethylhexyl acrylate.

The vinylaromatic monomer which may be present in the copolymer can be chosen from vinylaromatic monomers other than tert-butylstyrene, which is known to undergo radical-mediated polymerization. Vinylaromatic monomers which can be used in particular are those containing from 8 to 20 carbon atoms, and preferably those containing from 4 to 14 carbon atoms. Such monomers are, for example, styrene, 1-vinylnaphthalene, 2-vinylnaphthalene, 2-methylstyrene (or ortho-methylstyrene), 3-methylstyrene, 4-methylstyrene (or para-methylstyrene), 4-propylstyrene, 4-cyclohexylstyrene, 4-dodecylstyrene, 2-ethyl-4-benzylstyrene and 4-(phenylbutyl)styrene. Styrene, para-methylstyrene, ortho-methylstyrene and mixtures can preferably be used. The vinylaromatic monomer which is particularly preferred is para-methylstyrene.

Advantageously, the copolymer can be derived from the polymerization of:
a) 10 to 30% by weight of para-tert-butylstyrene,
b) 20 to 40% by weight of para-methylstyrene,
c) 25 to 45% by weight of isobutyl methacrylate, and
d) 8 to 25% by weight of 2-ethylhexyl acrylate.

According to a specific embodiment of the invention, the copolymer can be crosslinked and can thus comprise, in a known manner, at least one ethylenic crosslinking monomer. Crosslinking monomers which may be mentioned in particular are ethylene glycol dimethacrylate, ethylene glycol diacrylate and divinylbenzene. Ethylene glycol dimethacrylate is preferably used.

The crosslinking monomer can be present in the copolymer in an amount ranging from 0.1% to 10% by weight relative to the total weight of the mixture of monomers in the copolymer.

The copolymers of the composition according to the invention are known and are described in particular in U.S. Pat. No. 5,496,905, the disclosure of which is incorporated by reference herein. Such copolymers are sold under the names "Plioway® Ultra 200" and "Plioway® Ultra G 20," by the company Goodyear.

The copolymer can be present in the composition in an amount ranging from 0.5% to 30% by weight relative to the total weight of the composition, preferably from 1% to 20% by weight, and still more preferably from 5% to 15% by weight.

The fatty phase of the composition according to the invention makes it possible to incorporate the styrene/acrylate copolymer easily into the composition.

The fatty phase can comprise at least one fatty substance which may be liquid, pasty or solid at room temperature (in general 25° C.). In particular, the fatty substance can be chosen from oils, waxes, pasty fatty substances, gums and mixtures thereof. The fatty substance can be present in the composition in an amount ranging from 5% to 99% by weight relative to the total weight of the composition, preferably from 10% to 80% by weight, and more preferably from 20% to 75% by weight.

Advantageously, the fatty phase of the composition comprises at least one fatty substance which is liquid at room temperature.

The liquid fatty substance may be a volatile oil. The expression "volatile oil" means an oil capable of evaporating at room temperature from a support onto which it has been applied, in other words an oil which has a measurable vapor pressure at room temperature.

It is possible, in particular, to use one or more oils which are volatile at room temperature and atmospheric pressure having, for example, a vapor pressure, at room pressure and temperature, of >0 mmHg (0 Pa) and in particular ranging from $10^{-3}$ to 300 mmHg (0.13 Pa to 40,000 Pa), on condition that the boiling point is greater than 30° C. These volatile oils are favorable for obtaining a film with total "transfer-resistance" properties and good staying power. These volatile oils also facilitate the application of the composition onto the skin, mucous membranes and superficial body growths. These oils can be hydrocarbon-based oils, silicone-based oils, fluoro oils or mixtures thereof.

The expression "hydrocarbon-based oil" means an oil mainly containing hydrogen and carbon atoms. The preferred volatile hydrocarbon-based oils which are suitable for the composition according to the invention are, in particular, hydrocarbon-based oils containing from 8 to 16 carbon atoms, and in particular $C_8$–$C_{16}$ isoalkanes (or isoparaffins) and branched $C_8$–$C_{16}$ esters, such as isododecane (also known as 2,2,4,4,6-pentamethylheptane), isodecane, isohexadecane, isohexyl neopentanoate and mixtures thereof. Other volatile hydrocarbon-based oils, such as petroleum distillates, in particular those sold under the name Shell Solt by the company Shell, can also be used. Volatile hydrocarbon-based oils are particularly preferred since they allow good dissolution of the styrene/acrylate copolymer.

Volatile oils which can also be used are volatile silicones, such as, for example, volatile cyclic silicone oils, in particular those with a viscosity≦8 centistokes ($8\times10^{-6}$ m$^2$/s), such as octamethylcyclotetrasiloxane, decamethylcyclopentasiloxane, hexadecamethylcyclohexasiloxane, linear volatile silicones such as octamethyltrisiloxane, heptamethylhexyltrisiloxane, heptamethyloctyltrisiloxane and decamethyltetrasiloxane, or alternatively volatile fluoro oils such as nonafluoromethoxybutane or perfluoromethylcyclopentane.

The volatile oil can be present in the composition according to the invention in an amount ranging from 0% to 80% by weight, in particular from 1% to 80%, relative to the total weight of the composition, preferably from 0% to 65% by weight, and in particular from 1% to 65%.

The liquid fatty substance can also be chosen from non-volatile oils, and in particular non-volatile hydrocarbon-based and/or silicone-based and/or fluoro oils.

Non-volatile hydrocarbon-based oils which may be mentioned in particular are:

hydrocarbon-based oils of animal origin, such as perhydrosqualene;

hydrocarbon-based oils of plant origin, such as liquid triglycerides of fatty acids having 4 to 10 carbon atoms, such as triglycerides of heptanoic or octanoic acids, or alternatively sunflower oil, grapeseed oil, sesame oil, corn oil, apricot oil, castor oil, avocado oil, olive oil, cereal germ oil, soybean oil, sweet almond oil, palm oil, rapeseed oil, cotton oil, hazelnut oil, macadamia oil, jojoba oil, caprylic/capric acid triglycerides, such as those sold under the names Miglyol 810, 812 and 818 by the company Dynamit Nobel, and karite butter;

linear or branched hydrocarbons of mineral or synthetic origin, such as petroleum jelly, polydecenes and hydrogenated polyisobutene, such as parleam;

synthetic esters and ethers, such as the oils of formula $R_1COOR_2$ in which $R_1$ represents a higher fatty acid residue containing from 6 to 29 carbon atoms and $R_2$ represents a hydrocarbon-based chain containing from 3 to 30 carbon atoms, such as Purcellin oil, isopropyl myristate, isopropyl palmitate, butyl stearate, hexyl laurate, diisopropyl adipate, isononyl isononate, 2-ethylhexyl palmitate, 2-hexyldecyl laurate, 2-octyldecyl palmitate, and 2-octyldodecyl myristate or lactate; polyol esters, such as propylene glycol dioctanoate, neopentyl glycol heptanoate, diethylene glycol diisononanoate and pentaerythritol esters;

fatty alcohols which are liquid at room temperature, with a branched and/or unsaturated carbon chain containing from 12 to 26 carbon atoms, such as octyldodecanol, isostearyl alcohol, oleyl alcohol, 2-hexyldecanol, 2-butyloctanol and 2-undecylpentadecanol;

higher fatty acids, such as myristic acid, palmitic acid, stearic acid, behenic acid, oleic acid, linoleic acid, linolenic acid and isostearic acid; and mixtures thereof.

The non-volatile silicone oils which can be used in the composition according to the invention can be oils of low viscosity such as linear polysiloxanes whose degree of polymerization is preferably from about 6 to 2000. Mention may be made, for example, of polydimethylsiloxanes (PDMSs) with a viscosity of greater than 10 mPa.s, phenyl dimethicones, phenyl trimethicones, polyphenylmethylsiloxanes and mixtures thereof.

The non-volatile oils can be present in the composition according to the invention in an amount ranging from 0% to 5% by weight relative to the total weight of the composition, preferably from 0% to 2% by weight, and more preferably from 0.1 to 2% by weight.

The waxes can be chosen from waxes of animal origin, waxes of plant origin or waxes of synthetic origin.

The waxes which can be used in the composition according to the invention have, as a general rule, a melting point between 40 and 110° C. and a needle penetration ranging from 1 to 217. The needle penetration of waxes is determined according to French standard NF T 60-123 or U.S. standard ASTM D 1321, at a temperature of 25° C. According to these standards, needle penetration is the measurement of the depth, expressed in tenths of a millimeter, to which a standardized needle, weighing 2.5 g, placed in a mobile assembly weighing 97.5 g and placed on the wax to be tested for 5 seconds, penetrates into the wax.

Among the waxes of animal origin which may be mentioned are beeswaxes, lanolin waxes and Chinese insect waxes.

Among the waxes of plant origin which may be mentioned are rice waxes, carnauba wax, candelilla wax, ouricury wax, cork fibre waxes, sugarcane waxes, Japan waxes, sumac wax and cotton wax.

Among the waxes of mineral origin which may be mentioned are paraffins, microcrystalline waxes, montan waxes and ozokerites.

Among the waxes of synthetic origin which may be used in particular are polyolefin waxes and in particular polyethylene waxes, the waxes obtained by Fischer-Tropsch synthesis, waxy copolymers and esters thereof, and silicone waxes.

It is also possible to use hydrogenated oils of animal or plant origin which correspond to the two physical characteristics mentioned above.

Among these oils which may be mentioned are hydrogenated oils obtained by catalytic hydrogenation of fatty substances composed of a linear or non-linear $C_8$–$C_{32}$ fatty chain, hydrogenated sunflower oil, hydrogenated castor oil, hydrogenated coconut oil, hydrogenated jojoba oil, hydrogenated lanolin and hydrogenated palm oils.

The waxes which can be used according to the present invention are preferably solid and rigid at a temperature below 50° C.

The composition according to the invention can comprise from 0.1% to 30% by weight of wax, relative to the total weight of the composition, and preferably from 1% to 25% by weight.

Preferably, the composition according to the invention can comprise:

at least one wax with a needle penetration ranging from 1 to 7.5 (referred to as wax I), in particular in an amount ranging from 0.1% to 20% by weight relative to the total weight of the composition, and at least one wax with a needle penetration of greater than 7.5 and less than or equal to 217 (referred to as wax II), in particular in an amount ranging from 0.1% to 10% by weight relative to the total weight of the composition. This wax mixture is suitable in particular when the composition is intended for use as a mascara or an eyeliner.

The composition can also comprise at least one dyestuff, such as a pulverulent compound and/or a liposoluble dye, for example in a proportion of from 0.01 to 50% of the total weight of the composition. The pulverulent compounds can be chosen from the pigments, nacres and fillers usually used in cosmetic or dermatological compositions. Advantageously, the pulverulent compounds represent from 0.1 to 25% of the total weight of the composition, and preferably from 1 to 20%. When the composition is in powder form, it can contain up to 95% by weight of pulverulent compounds.

The pigments can be white or colored, and inorganic and/or organic. Among the inorganic pigments, mention may be made of titanium dioxide, which can be optionally surface-treated, zirconium oxide or cerium oxide, as well as iron oxides or chromium oxide, manganese violet, ultramarine blue, chromium hydrate and ferric blue. Among the organic pigments which may be mentioned are carbon black, pigments of D & C type, and lakes based on cochineal carmine, barium, strontium, calcium and aluminium.

The nacreous pigments can be chosen from white nacreous pigments such as mica coated with titanium or with bismuth oxychloride, colored nacreous pigments such as titanium mica with iron oxides, titanium mica with, in particular, ferric blue or chromium oxide, titanium mica with an organic pigment of the abovementioned type, as well as nacreous pigments based on bismuth oxychloride.

The fillers can be chosen from those which are well known to those skilled in the art and which are commonly used in cosmetic compositions.

The composition can also comprise one or more cosmetic, dermatological, hygiene or pharmaceutical active agents, such as moisturizers, vitamins, essential fatty acids, proteins, ceramides, sunscreens, free-radical scavengers, anti-inflammatory agents or tanning agents. Needless to say, a person skilled in the art will take care to select this or these optional additional compounds, and/or the amount thereof, such that the advantageous properties of the composition according to the invention are not, or are not substantially, adversely affected by the addition envisaged. These active agents can be used, for example, in an amount ranging from 0.001% to 20% by weight, relative to the total weight of the composition.

The composition according to the invention can moreover comprise, depending on the type of use envisaged, the constituents conventionally used in the fields under consideration, which are present in an amount that is suitable for the desired usage form.

The composition can also contain any additive usually used in such compositions, such as thickeners, fragrances, preserving agents, surfactants, lipophilic or hydrophilic film-forming polymers which are dissolved or dispersed in the composition, in particular dispersed in an aqueous medium or an oily medium, as described in European patent application nos. EP-A-749,747 and EP-A-749,746.

When the fatty phase of the composition according to the invention comprises at least one fatty substance which is liquid at room temperature, the composition can also comprise a thickener for the fatty phase. The thickener can be chosen from organomodified clays, which are clays treated with compounds chosen in particular from quaternary amines and tertiary amines. Organomodified clays which may be mentioned are organomodified bentonites such as those sold under the name "Bentone 34" by the company Rheox, and organomodified hectorites such as those sold under the name "Bentone 27" and "Bentone 38" by the company Rheox. Fat-soluble alkylated guar gums and treated silicas can also be used.

According to one embodiment of the invention, the composition can advantageously be anhydrous, and can contain less than 10% water relative to the total weight of the composition. In this case, it can be in the form of an oily gel, an oily liquid, a paste, a product cast as a stick or tube, or in a dish, or alternatively in the form of a powder.

According to another embodiment, the composition can also comprise at least one aqueous phase and, in this case, can be in the form of a water-in-oil, oil-in-water, wax-in-water or water-in-wax emulsion, or a vesicular dispersion containing ionic and/or nonionic lipids. The water content can range from 10% to 95% by weight relative to the total weight of the composition.

These compositions for topical application can in particular constitute a cosmetic, dermatological, hygiene or pharmaceutical composition for protecting, caring for or treating the skin, in particular for the face, the neck, the hands or the body (for example a care cream, an antisun oil or a body gel), a make-up composition, an antisun composition or an artificial tanning composition.

The make-up composition can be, in particular, a mascara, an eyeliner, a product for the lips (e.g., lipstick), a nail varnish, an eyeshadow, a face powder, a concealer product, a foundation or a make-up product for the body, such as a temporary or semi-permanent tattoo.

The invention is illustrated in greater detail in the examples below.

EXAMPLE 1

| A mascara having the composition below was prepared: | |
|---|---|
| beeswax | 2.6 g |
| carnauba wax | 1.3 g |
| paraffin wax | 7.3 g |
| Plioway ® Ultra 200 copolymer from Goodyear | 10 g |
| stearic acid | 5.24 g |
| triethanolamine | 2.16 g |
| 2-amino-2-methyl-1,3-propanediol | 0.45 g |
| water-soluble thickeners | 3.92 g |
| water-soluble film-forming polymers | 0.99 g |
| Pigments | 4 g |
| Preserving agents qs | |
| water qs | 100 g |

Plioway® Ultra 200 is a para-tert-butylstyrene/para-methylstyrene/2-ethylhexyl acrylate/isobutyl methacrylate copolymer. It can be replaced with Plioway® Ultra G 20 which is a para-tert-butylstyrene/para-methylstyrene/2-ethylhexyl acrylate/isobutyl methacrylate/ethylene glycol dimethacrylate copolymer.

The mascara applied easily to the eyelashes and made it possible to obtain a make-up effect which had good staying power for longer than one day and which was water-resistant.

EXAMPLE 2

| An eyeliner having the composition below was prepared: | |
|---|---|
| waxes | 6.9 g |
| pigments | 10 g |
| thickener | 7 g |
| Plioway ® Ultra 200 copolymer | 10 g |
| vinyl acetate/allyl stearate copolymer (65/35) (liposoluble polymer) | 6 g |
| rice starch | 0.95 g |
| light paraffinic and naphthenic hydrocarbons (Shell Solt from Shell) qs | 100 g |

A waterproof eyeliner was obtained which applied easily to the edge of the eyelids and, after having been applied, left a homogeneous film which had good staying power over time and good resistance to water and to perspiration. The film did not degrade during the day and did not transfer.

EXAMPLE 3

| A mascara having the composition below was prepared: | |
|---|---|
| paraffin wax | 2 g |
| carnauba wax | 4.2 g |
| beeswax | 7.4 g |
| polyvinyl laurate (Mexomer PP from Chimex) | 0.66 g |
| vinyl acetate/allyl stearate copolymer (65/35) | 1.96 g |
| Plioway ® Ultra G 20 copolymer from Goodyear | 10 g |
| polymer in aqueous dispersion* | 2.5 g AM |
| rice starch | 0.74 g |
| pigments | 5 g |
| preserving agents qs | |
| isododecane qs | 100 g |

*Vinyl acetate/crotonic acid/vinyl 4-tert-butylbenzoate copolymer (65/10/25) neutralized to 65% with 2-amino-2-methyl-1-propanol and plasticized to 25% with diisopropyl adipate, prepared according to the teaching of European patent application no. EP-A-665,234, the disclosure of which is incorporated herein by reference.

The mascara applied easily to the eyelashes and had good staying power throughout the day. The make-up effect obtained was water-resistant and did not transfer.

What is claimed is:

1. A composition for topical application comprising, in a cosmetically, dermatologically, hygienically or pharmaceutically acceptable support, at least one fatty phase and at least one lipophilic polymer, wherein said lipophilic polymer is a tert-butylstyrene/$C_1$–$C_{10}$ alkyl methacrylate/$C_1$–$C_{10}$ alkyl acrylate copolymer.

2. The composition according to claim 1, wherein said lipophilic polymer is a copolymer of tert-butylstyrene/$C_1$–$C_{10}$ alkyl methacrylate/$C_1$–$C_{10}$ alkyl acrylate and of a vinylaromatic monomer other than tert-butylstyrene.

3. The composition according to claim 2, wherein said lipophilic polymer is a copolymer derived from the polymerization of:
   a) from 10 to 55% by weight, relative to the total weight of monomers, of para-tert-butylstyrene;
   b) from 20 to 80% by weight of $C_1$–$C_{10}$ alkyl methacrylate monomer;
   c) from 2 to 25% by weight of $C_1$–$C_{10}$ alkyl acrylate monomer; and
   d) from 0 to 40% by weight of vinylaromatic monomer other than para-tert-butylstyrene.

4. The composition according to claim 1, wherein said alkyl methacrylate contains an alkyl radical having from 1 to 4 carbon atoms.

5. The composition according to claim 4, wherein said alkyl methacrylate is isobutyl methacrylate.

6. The composition according claim 1, wherein said alkyl acrylate contains an alkyl radical having from 2 to 8 carbon atoms.

7. The composition according claim 6, wherein said alkyl acrylate is 2-ethylhexyl acrylate.

8. The composition according claim 2, wherein said vinylaromatic monomer contains from 4 to 14 carbon atoms.

9. The composition according claim 8, wherein said vinylaromatic monomer is selected from styrene, para-methylstyrene, ortho-methylstyrene and mixtures thereof.

10. The composition according claim 9, wherein said vinylaromatic monomer is para-methylstyrene.

11. The composition according claim 3, wherein said lipophilic polymer comprises:
   a) from 10 to 30% by weight of para-tert-butylstyrene;
   b) from 20 to 40% by weight of para-methylstyrene;

c) from 25 to 45% by weight of isobutyl methacrylate; and d) from 8 to 25% by weight of 2-ethylhexyl acrylate.

12. The composition according claim 11, wherein said lipophilic polymer comprises:

a) from 15 to 25% by weight of para-tert-butylstyrene;

b) from 25 to 35% by weight of para-methylstyrene;

c) from 30 to 40% by weight of isobutyl methacrylate; and d) from 10 to 20% by weight of 2-ethylhexyl acrylate.

13. The composition according claim 1, wherein said copolymer further comprises at least one ethylenic crosslinking monomer.

14. The composition according claim 13, wherein said crosslinking monomer is ethylene glycol dimethacrylate.

15. The composition according claim 1, wherein said copolymer is present in an amount ranging from 0.5% to 30% by weight relative to the total weight of the composition.

16. The composition according claim 15, wherein said copolymer is present in an amount ranging from 1% to 30% by weight relative to the total weight of the composition.

17. The composition according claim 16, wherein said copolymer is present in an amount ranging from 5% to 15% by weight relative to the total weight of the composition.

18. The composition according claim 1, wherein said fatty phase comprises at least one fatty substance chosen from oils, waxes, gums and pasty fatty substances of animal, plant, mineral or synthetic origin.

19. The composition according claim 18, wherein said fatty phase comprises at least one fatty substance present in an amount ranging from 5% to 99% by weight relative to the total weight of the composition.

20. The composition according claim 19, wherein said fatty phase comprises at least one fatty substance present in an amount ranging from 10% to 80% by weight relative to the total weight of the composition.

21. The composition according claim 20, wherein said fatty phase comprises at least one fatty substance present in an amount ranging from 20% to 75% by weight relative to the total weight of the composition.

22. The composition according claim 18, wherein said fatty phase comprises at least one volatile oil.

23. The composition according claim 22, wherein said at least one volatile oil is a hydrocarbon containing oil.

24. The composition according claim 23, wherein said hydrocarbon containing oil is chosen from $C_8$–$C_{16}$ isoalkanes and branched $C_8$–$C_{16}$ esters.

25. The composition according claim 22, wherein said at least one volatile oil is present in an amount ranging from 1% to 80%, relative to the total weight of the composition.

26. The composition according claim 25, wherein said at least one volatile oil is present in an amount ranging from 1% to 65%, relative to the total weight of the composition.

27. The composition according claim 18, wherein said fatty phase comprises at least one wax.

28. The composition according claim 27, wherein said at least one wax is present in an amount ranging from 0.1% to 30%, relative to the total weight of the composition.

29. The composition according claim 28, wherein said at least one wax is present in an amount ranging from 1% to 25%, relative to the total weight of the composition.

30. The composition according claim 1, further comprising at least one dyestuff.

31. The composition according claim 30, wherein said at least one dyestuff comprises at least one pulverulent compound chosen from fillers, pigments, nacres and mixtures thereof.

32. The composition according claim 1, further comprising at least one active agent chosen from cosmetic, dermatological, hygiene and pharmaceutical active agents.

33. The composition according claim 1, further comprising at least one additive chosen from thickeners, fragrances, preserving agents, surfactants and lipophilic or hydrophilic film-forming polymers which are dissolved or dispersed in the composition.

34. The composition according claim 1, wherein said composition is in the form of a stick, tube, dish, soft paste, oily gel, oily liquid or a powder.

35. The composition according claim 34, wherein said soft paste has a dynamic viscosity at 25° C. from about 1 to 40 Pa.s.

36. The composition according claim 1, wherein said composition is anhydrous.

37. The composition according claim 1, wherein said composition is in the form of a water-in-oil emulsion, an oil-in-water emulsion, or a vesicular dispersion containing ionic and/or nonionic lipids.

38. A skin-care or skin make-up product for caring for and/or making up the skin and/or superficial keratinous body growths, said product comprising the cosmetic composition according to claim 1.

39. The product according to claim 38, wherein said product is in the form of a mascara, an eyeliner, a face powder, an eyeshadow, a lip composition, a concealer, a make-up product for the body, a composition for protecting, caring for or treating the skin, an anti-sun composition or an artificial tanning composition.

40. A method for caring for or making up the skin and/or superficial keratinous body growths, said method comprising applying to the skin and/or superficial keratinous body growths a composition to obtain a film on said skin and/or superficial body growths, said composition comprising at least one lipophilic polymer, and at least one fatty phase, wherein said lipophilic polymer is tert-butylstyrene/ $C_1$–$C_{10}$ alkyl methacrylate/$C_1$–$C_{10}$ alkyl acrylate copolymer, and wherein said film has good staying power and/or is resistant to water, to rubbing, to perspiration, and/or to sebum, and/or which has transfer-resistance properties.

41. The method according to claim 40, wherein said lipophilic polymer is a copolymer of tert-butylstyrene/ $C_1$–$C_{10}$ alkyl methacrylate/$C_1$–$C_{10}$ alkyl acrylate and of a vinylaromatic monomer other than tert-butylstyrene.

42. The method according to claim 41, wherein said lipophilic polymer comprises:

a) from 10 to 55% by weight, relative to the total weight of monomers, of para-tert-butylstyrene;

b) from 20 to 80% by weight of $C_1$–$C_{10}$ alkyl methacrylate monomer;

c) from 2 to 25% by weight of $C_1$–$C_{10}$ alkyl acrylate monomer; and d) from 0 to 40% by weight of vinylaromatic monomer other than para-tert-butylstyrene.

43. The method according to claim 40, wherein said alkyl methacrylate contains an alkyl group having from 1 to 4 carbon atoms.

44. The method according to claim 43, wherein said alkyl methacrylate is isobutyl methacrylate.

45. The method according to claim 40, wherein said alkyl acrylate contains an alkyl group having from 2 to 8 carbon atoms.

46. The method according to claim 45, wherein said alkyl acrylate is 2-ethylhexyl acrylate.

47. The method according to claim 41, wherein said vinylaromatic monomer contains from 4 to 14 carbon atoms.

48. The method according to claim 47, wherein said vinylaromatic monomer is chosen from styrene, para-methylstyrene, ortho-methylstyrene and mixtures thereof.

49. The method according to claim 48, wherein said vinylaromatic monomer is para-methylstyrene.

50. The method according to claim 42, wherein said lipophilic polymer comprises:
   a) from 10 to 30% by weight of para-tert-butylstyrene;
   b) from 20 to 40% by weight of para-methylstyrene;
   c) from 25 to 45% by weight of isobutyl methacrylate; and
   d) from 8 to 25% by weight of 2-ethylhexyl acrylate.

51. The method according to claim 50, wherein said lipophilic polymer comprises:
   a) from 15 to 25% by weight of para-tert-butylstyrene;
   b) from 25 to 35% by weight of para-methylstyrene;
   c) from 30 to 40% by weight of isobutyl methacrylate; and
   d) from 10 to 20% by weight of 2-ethylhexyl acrylate.

52. The method according to claim 40, wherein said lipophilic polymer further comprises at least one ethylenic crosslinking monomer.

53. The method according to claim 52, wherein said crosslinking monomer is ethylene glycol dimethacrylate.

54. A composition for topical application comprising, in a cosmetically, dermatologically, hygienically or pharmaceutically acceptable support, at least one fatty phase and at least one lipophilic polymer,
   wherein said lipophilic polymer is a tert-butylstyrene/ $C_1$–$C_{10}$ alkyl methacrylate/$C_1$–$C_{10}$ alkyl acrylate copolymer; and
   wherein said copolymer is present in an amount ranging from 0.5% to 30% by weight relative to the total weight of the composition, and comprises:
      a) from 10 to 30% by weight of para-tert-butylstyrene,
      b) from 20 to 40% by weight of para-methylstyrene,
      c) from 25 to 45% by weight of isobutyl methacrylate, and
      d) from 8 to 25% by weight of 2-ethylhexyl acrylate.

55. A method for caring for or making up the skin and/or superficial keratinous body growths, said method comprising:
   applying to the skin and/or superficial keratinous body growths a composition to obtain a film on said skin and/or superficial body growths, said composition comprising
   at least one lipophilic polymer, and
   at least one fatty phase,
   wherein said lipophilic polymer is tert-butylstyrene/ $C_1$–$C_{10}$ alkyl methacrylate/$C_1$–$C_{10}$ alkyl acrylate copolymer;
   wherein said film has good staying power and/or is resistant to water, to rubbing, to perspiration, and/or to sebum, and/or which has transfer-resistance properties; and
   wherein said copolymer is present in an amount ranging from 0.5% to 30% by weight relative to the total weight of the composition, and comprises:
      a) from 10 to 30% by weight of para-tert-butylstyrene,
      b) from 20 to 40% by weight of pata-methylstyrene,
      c) from 25 to 45% by weight of isobutyl methacrylate, and
      d) from 8 to 25% by weight of 2-ethylhexyl acrylate.

* * * * *

UNITED STATES PATENT AND TRADEMARK OFFICE
CERTIFICATE OF CORRECTION

PATENT NO. : 6,325,994 B1  
DATED : December 4, 2001  
INVENTOR(S) : Nathalie Collin et al.

Page 1 of 1

It is certified that error appears in the above-identified patent and that said Letters Patent is hereby corrected as shown below:

<u>Column 12, claim 55,</u>  
Line 29, "pata-methylstyrene" should read -- para-methylstyrene --.

Signed and Sealed this

Ninth Day of April, 2002

Attest:

Attesting Officer

JAMES E. ROGAN  
*Director of the United States Patent and Trademark Office*